United States Patent [19]

Parsons et al.

[11] Patent Number: 5,070,011
[45] Date of Patent: Dec. 3, 1991

[54] DNA PROBES FOR THE DETECTION OF *HAEMOPHILUS DUCREYI* AND METHOD OF USE

[75] Inventors: Linda M. Parsons, Voorheesville; Lawrence Bopp, Scotia; Alfred L. Waring, Saratoga Springs; Mehdi Shayegani, Delmar, all of N.Y.

[73] Assignee: Health Research Inc., Albany, N.Y.

[21] Appl. No.: 367,024

[22] Filed: Jun. 16, 1989

[51] Int. Cl.$^5$ .................. C12Q 1/68; G01N 33/566; C07H 15/12; C07H 17/00

[52] U.S. Cl. .......................... 435/6; 436/94; 436/501; 536/26; 536/27; 536/28

[58] Field of Search .............. 435/6, 172.3; 436/501, 436/94; 536/27

[56] References Cited

U.S. PATENT DOCUMENTS 4,358,535  11/1982  Falkow et al. .................... 435/6
4,374,925  2/1983   Litman et al. .................... 435/7
4,740,467  4/1988   Kettman et al. ................... 435/7
4,810,644  3/1989   Tchen et al. ..................... 435/91

*Primary Examiner*—Robert A. Wax
*Assistant Examiner*—Eric Steffe
*Attorney, Agent, or Firm*—Cooper & Dunham

[57] ABSTRACT

This invention provides DNA probes which are useful for the detection of *Haemophilus ducreyi*. This invention also provides a method of detecting in a subject the presence of *H. ducreyi* which comprises obtaining a suitable sample from the subject, denaturing the DNA in the sample so as to produce single stranded DNA molecules, contacting the single stranded DNA molecules so obtained with a single stranded oligonucleotide probe, under suitable conditions which permit hybridization of complementary single stranded molecules, and detecting the presence of hybridized molecules, whereby the presence of *H. ducreyi* in the subject is detected. This invention further comprises a kit which is useful for the detection of *H. ducreyi*.

16 Claims, 15 Drawing Sheets

FIGURE 1 A

Bacterial suspension

RESULTS WITH PROBE:[A]

HAEMOPHILUS DUCREYI:[B]

| | pLP1 | pLP4 | pLP8 |
|---|---|---|---|
| ATCC 27721 | ++++ | ++++ | ++++ |
| ATCC 27722 | ++++ | ++++ | ++++ |
| ATCC 33921 | ++++ | ++++ | ++++ |
| ATCC 33922 | ++++ | ++++ | ++++ |
| ATCC 33940 | +++ | ++++ | +++ |
| CDC 542 | ++++ | ++++ | ++++ |
| CDC 844 | ++++ | ++++ | ++++ |
| Nine clinical isolates from New York City, 1988 | ++++[C] | ++++[C] | ++++ |

FIGURE 1 B

OTHER ORGANISMS:

| D | | | |
|---|---|---|---|
| Acinetobacter calcoaceticus subsp. twoffii B277 | - | - | - |
| Actinobacillus actinomyce-temcomitans B1083 | ND | ND | - |
| Actinomyces species strain B1228 | - | - | - |
| Alcaligenes faecalis B38-78 | - | - | - |
| Bacteroides fragilis ATCC 25285 | - | - | - |
| Clostridium perfringens ATCC 13124 | - | - | - |
| Corynebacterium diphthe-riae C5703 | - | - | - |
| Escherichia coli ATCC 25922 | - | - | - |
| Garderella vaginalis ATCC 14018 | - | - | - |

FIGURE 1 C

| | | | |
|---|---|---|---|
| G. vaginalis B1905 (atypical) | – | – | – |
| Haemophilus haemoglobin-ophilus B1701 | ND | ND | Weak |
| H. influenzae, type A | Weak | Weak | Weak |
| H. influenzae, type B | Weak | Weak | Weak |
| H. influenzae, nontypeable, biotype III | ND | ND | Weak |
| H. influenzae, nontypeable, biotype III | ND | ND | Weak |
| H. influenzae, nontypeable, biotype IV | ND | ND | Weak |
| H. parainfluenzae B1134 | Weak | Weak | Weak |
| Lactobacillus acidophilus ATCC 4962 | – | – | – |
| Moraxella oslaensis B1596 | – | – | – |
| Neisseria gonorrhoeae 116 | – | – | – |

FIGURE 1 D

| | | | |
|---|---|---|---|
| N. lactamica B2159 | - | | - |
| N. meningitidis W135 | - | - | - |
| Pasteurella haemolytica M6169 | ND | ND | - |
| P. gallinarum B697 | ND | ND | Weak |
| P. multocida B1221-76 | ND | ND | Weak |
| P. pneumotropica M5354 | ND | ND | Weak |
| Peptostreptococcus anaerobius A943 | - | - | - |
| Proteus mirabilis | - | - | - |
| Pseudomonas aeruginosa ATCC 27853 | - | - | - |
| Staphylococcus coagulase-negative strain B778 | - | - | - |
| Streptococcus agalactiae B2545 | - | - | - |
| S. bovis B1450 | - | - | - |
| S. faecalis ATCC 29212 | - | - | - |
| S. mutans B1254 | - | - | - |

FIGURE 1 E

| | | | | |
|---|---|---|---|---|
| S. sanguis II B1508 | - | - | - | - |
| Yersinia enterocolitica ATCC 9610 | ND | ND | - | - |
| Y. rohdei CDC 3022 | ND | ND | - | - |
| Other Samples: | | | | |
| DNA from all five H. ducreyi ATCC strains | ++++ | ++++ | ++++ | ++++ |
| Herpes simplex virus type 2-infected cells | ND | ND | - | - |
| Treponema pallidum in rabbit testicular fluid | ND | ND | - | - |

FIGURE 2 A

RESULTS WITH PROBE[A]:

| NO. OF CFU OF H. DUCREYI/ WELL PURE CULTURES[B] | pLP8 | Fragment 1, 4 or 8 |
|---|---|---|
| $4.9 \times 10^6$ | 4+ | ND |
| $4.9 \times 10^5$ | 3+ | ND |
| $4.9 \times 10^4$ | 1-2+ | ND |
| $4.9 \times 10^3$ | Weak | ND |
| $1.4 \times 10^7$ | ND | 2-3+ |
| $1.4 \times 10^6$ | ND | 2-3+ |
| $1.4 \times 10^5$ | ND | 1-2+ |
| $1.4 \times 10^4$ | ND | Weak-1+ |
| $1.4 \times 10^3$ | ND | Negative |

FIGURE 2 B

| MIXED CULTURES C | | |
|---|---|---|
| 4.7 x 10$^6$ | ND | 3+ |
| 4.7 x 10$^5$ | ND | 2+ |
| 4.7 x 10$^4$ | ND | Weak-1+ |
| 4.7 x 10$^3$ | ND | Negative-weak |
| 4.7 x 10$^2$ | ND | Negative-weak |

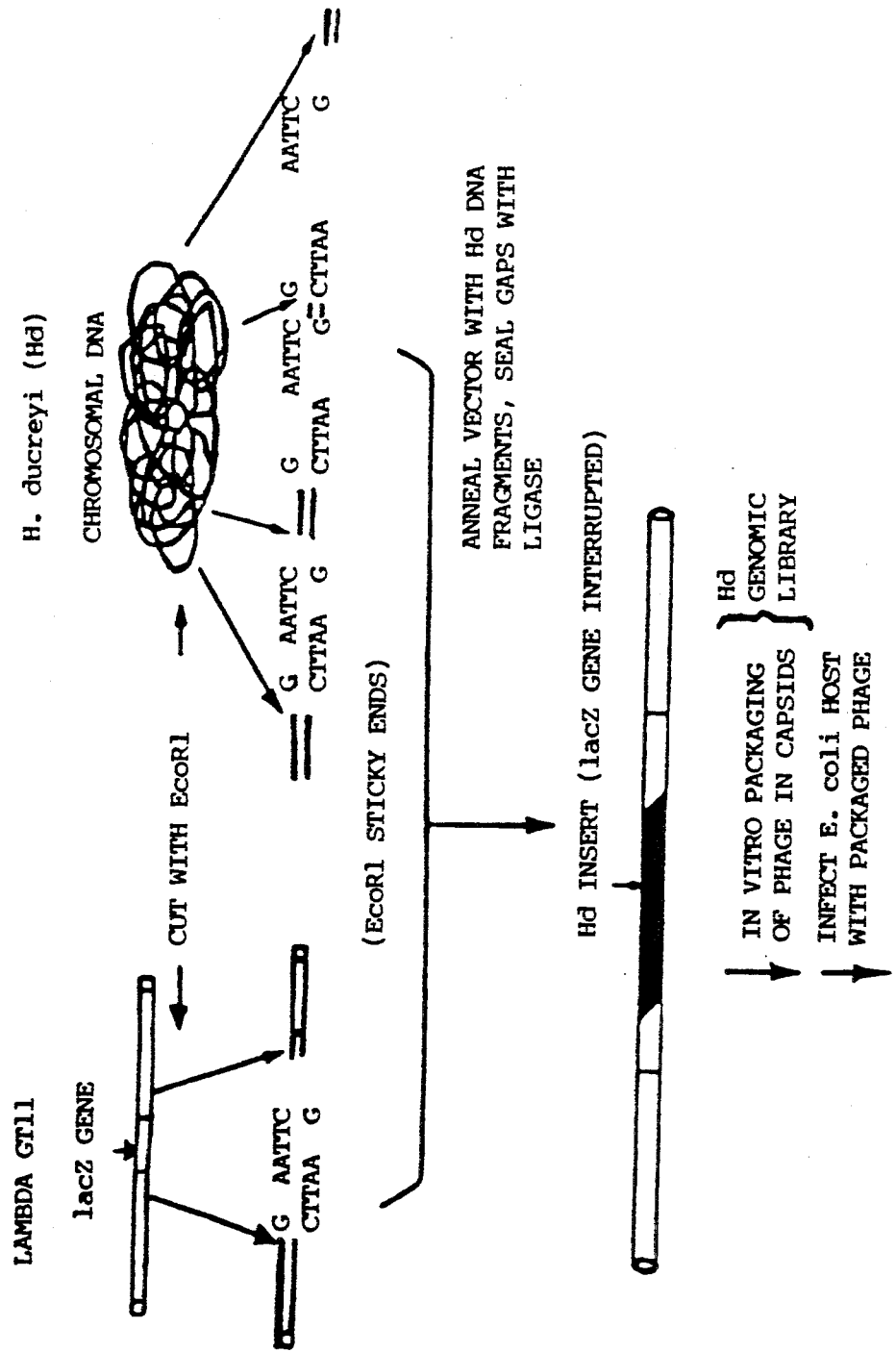

DNA PROBES FOR THE DETECTION OF *HAEMOPHILUS DUCREYI* AND METHOD OF USE

BACKGROUND OF THE INVENTION

Chancroid is a human sexually transmitted disease caused by *Haemophilus ducreyi* and characterized by painful genital ulcers. The primary ulcer is often followed by multiple lesions which result in ulcers of various ages that can extend the duration of the illness to 1 to 3 months if appropriate treatment is not given (37). More than 50% of the cases progress to inguinal lymph node involvement manifested by buboes(37). Without treatment, the bubo can persist for many months. Infections with other pathogens such as *Treponema pallidum*, herpes simplex virus type 2, *Chlamydia trachomatis* (*lymphogranuloma venereum*), and *Calymmatobacterium granulomatis* (*granuloma inguinale*) can result in ulcerations clinically indistinguishable from those caused by *H. ducreyi*. Thus, accurate diagnosis of the etiologic agent is very important, since antimicrobial treatment for those different sexually transmitted diseases must be specific.

Open chancroidal lesions may enhance transmission of human immunodeficiency virus. Recent studies in Africa have established a significant association between history of genital ulceration and human immunodeficiency virus seropositivity (24, 30, 35). Since chancroid has been reported to be the most common cause of genital ulcers in Africa (12), this disease has been correlated specifically with heterosexual transmission of human immunodeficiency virus (35). These studies, together with the clinical observation that untreated ulcers can persist for months, highlight the importance of an accurate diagnosis which will lead to appropriate therapy.

*H. ducreyi* is a fastidious, slow-growing, gram-negative bacillus. Colonies grown on solid media vary in size, perhaps because of the peculiar cohesiveness of the organism, with larger colonies arising from more than one cell. Moreover, *H. ducreyi* remains tightly autoagglutinated when suspended in liquid. This cohesiveness has ruled out identification of the organism by serological agglutination tests, and difficulties in interpretation of fluorescent-antibody tests (due to bacterial clumping) have also been reported with both polyclonal (14) and monoclonal antibodies (33).

To maintain viability of the bacteria, *H. ducreyi* must be cultured within 4 to 6 hours after removal from the patient. Even when inoculated immediately, the organism does not grow well on most laboratory media, and recovery rates for clinical specimens have traditionally been poor. In 1978, Hammond et al. (19) reported the development of a selective enrichment agar. Use of this medium or adaptations of it (36) have led to significantly higher recovery rates of *H. ducreyi* in recent years. However, isolation rates of only 60 to 70% are still the norm for patients with clinically diagnosed chancroid (26).

During the past decade, outbreaks of chancroid have been reported in both Canada and the United States (3, 4, 8, 9, 20, 21, 27). In New York City, outbreaks have been reported yearly, beginning in 1981 (10) and the number of cases has been increasing each year since then. In 1987, over 62% (3,116 of 4,998) of the chancroid cases reported in the United States were from New York City (11).

In summary, the increasing incidence of chancroid is a matter of serious concern not only because of the problems of chancroidal disease itself, but also because this disease has been associated with heterosexual transmission of human immunodeficiency virus in Africa. Difficulties in clinical and laboratory diagnosis can interfere with an accurate identification of chancroid or its etiologic agent.

DNA probes for the detection of microorganisms, particularly Legionellas, have been described in the literature. (38) These compositions are obtained from the whole genomes of *Legonella pneumophila*, which are fragmented by a restriction endonuclease, and from these fragments are eliminated those sequences which are susceptible to being transcribed to ribosomal RNA.

Other methods which may be useful for the detection of *H. ducreyi* also have been disclosed. These methods, however, do not utilize specific DNA probes. One such method uses protein binding assays as the method of detection. (39) Another method uses monoclonal antibodies. (40)

SUMMARY OF THE INVENTION

It is an object of this invention to provide an accurate diagnostic test to identify the presence of *H. ducreyi* in a sample from a subject.

This invention provides DNA probes which are useful for the detection of *Haemophilus ducreyi*.

This invention also provides a method of detecting in a sample from a subject the presence of *H. ducreyi* which comprises denaturing the nucleic acid in the sample so as to produce single stranded nucleic acid molecules, contacting the single stranded nucleic acid molecules so obtained with a labelled single stranded oligonucleotide probe, under suitable conditions permitting hybridization of complementary single stranded molecules, and detecting the presence of hybridized molecules, whereby the presence of *H. ducreyi* in the subject is detected. A kit which is useful for the detection of *H. ducreyi* also is disclosed.

BRIEF DESCRIPTION OF THE FIGURES

FIGS. 1A through 1E list the organisms tested with the probes pLP1, pLP4, and pLP8 and the results obtained. The figure legend is as follows. "A"—the intensities of the bands (following 24 to 48 hours of exposure to X-ray film) compared and degrees of intensity were determined visually. "ND"—not determined. "B"—approximately $1.6 \times 10^4$ CFU per well. "C"—two of the none clinical isolates from New York City were tested. "D"—Approximately $3 \times 10^7$ to $6 \times 10^7$ CFU per well. These isolates were obtained from the lyophilized collection of the Laboratories for Bacteriology—New York State Department of Health.

FIGS. 2A and 2B illustrates the sensitivities of the probes. The figure legend for FIG. 2 is as follows. "A'-'"—the intensities of the bands (following 24 to 48 hours of exposure to X-ray film) were compared and degrees of intensity were determined visually. "ND"—not determined. "B"—ATCC 33922 was used. "C"—similar results from two experiments were combined. In the first experiment, the mixed culture consisted of 74% *H. ducreyi* ATCC 33922, 24% *H. influenzae* B, and 5% *E. Coli*; the second mixture consisted of 96% *H. ducreyi*, 4% *Proteus mirabilis*, and 0.1% *Staphylococcus epidermidis*.

FIG. 5A to 5C schematically illustrate isolation of *H. ducreyi* specific DNA sequences.

DETAILED DESCRIPTION OF THE INVENTION

Figure 3:
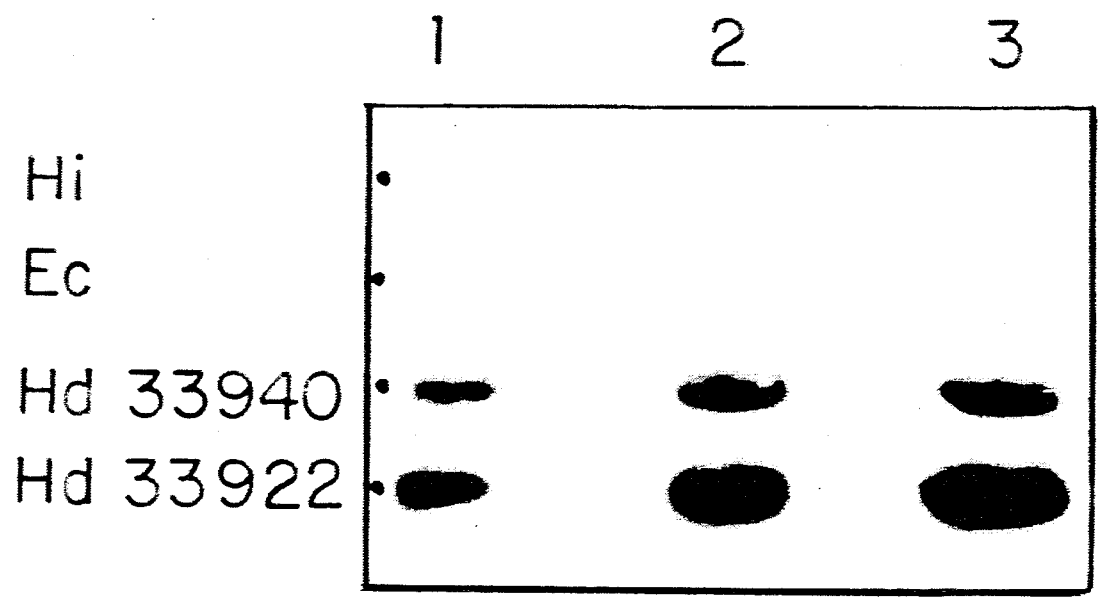
FIG. 3 shows the specificity of pLP8 probe.

For example, the *H. ducreyi* insert of plasmid pLP8 is cut with EcoR1 and separated from pUC13 by agarose gel electrophoresis.

The resulting 5.7 kb *H. ducreyi* insert is cut from the gel and purified. The insert is then labelled with $^{32}P$ by nick translation to a specific activity of about $10^8$ cpm/$\mu$g DNA. Unicorporated nucleotides may be separated from incorporated $^{32}P$ by column chromatography. Strands are separated by boiling.

For preparation of the samples, bacterial or DNA suspension of the sample are loaded onto nitrocellulose filters, and the liquid is removed by vacuum. The nitrocellulose filter is then removed and placed on blotting papers saturated sequentially with 10% SDS (cell lysis), denaturing solution (separation of the DNA strands), neutralizing solution and 2×SSPE. Filters are then dried for 2 hours at 80° C. under vacuum.

Hybridization may occur as follows. Baked nitrocellulose (containing sample) should be prehybridized with gentle agitation for 3 hours at 65° C. in buffer with Salmon Sperm DNA. Labelled probe ($10^5$ cpm/ml) is added after prehybridization. The filter is then sealed and allowed to hybridize overnight with gentle agitation at 65° C. In the morning, remove the probe and wash filter for 3 to 4 hours at 70° C. in 0.1×SSC and 0.1% SDS (stringent conditions). Air dry the filter. Expose the filter to X-ray film for about 24 to 48 hours at −70° C. and develop the film. Dark bands on the film indicate the presence of *H. ducreyi* in the sample.

This invention provides DNA probes which comprise from about 1.0 kb to 6.0 kb DNA purified from EcoRI digested chromosomal DNA from the bacterium *Haemophilus ducreyi* (ATCC 33922). Specifically, the probes are 1.5 kb, 5.4 kb and 5.7 kb EcoRI DNA fragments. Alternatively, the invention provides single stranded oligonucleotide probes which are complementary to *H. ducreyi* DNA. These oligonucleotide probes may be synthesized according to *H. ducreyi* sequence information.

This invention also provides the plasmids designated pLP1 (ATCC No. 68008), pLP4 (ATCC No. 68009), and pLP8 (ATCC No. 68010). The recombinant plasmids, i.e., pLP1, pLP4, and pLP8, were deposited on June 13, 1989 pursuant to the Budapest Treaty On The International Recognition Of The Deposit Of Microorganisms For The Purposes Of Patent Procedure with the Patent Culture Depository of the American Type Culture Collection (ATCC), 12301 Parklawn Drive, Rockville, Md. 20852 U.S.A. under ATCC Accession Nos. 68008, 68009, and 68010, respectively.

This invention further provides the DNA probes described hereinabove which are labelled with a detectable moiety, e.g. $^{32}P$, enzymes, fluorescent and luminescent molecules.

This invention further comprises a method of detecting in a subject the presence of *Haemophilus ducreyi* which comprises obtaining a suitable sample from the subject, denaturing the nucleic acid, i.e., DNA or RNA, in the sample so as to produce single stranded nucleic acid molecules, contacting the single stranded nucleic acid molecules so obtained with a single stranded oligonucleotide probe e.g., a labelled single stranded oligonucleotide probe described hereinabove or a single stranded probe produced by denaturing a DNA probe labelled with a detectable moiety, under suitable conditions permitting hybridization of complementary single stranded molecules, and detecting the presence of hybridized molecules, whereby the presence of *Haemophilus ducreyi* in the subject is detected. This invention further comprises amplifying the total DNA in the sample by culturing the organism. Alternatively, specific *Haemophilus ducreyi* DNA sequences may be amplified by methods such as the polymerase chain reaction.

The DNA probes which are useful in the practice of this invention are any DNA molecules which are capable of hybridizing to single stranded *H. ducreyi* DNA or RNA which is present in a sample. Such probes comprise, but are not limited to, the 1.5, 5.4, and 5.7 kb DNA probes and the single stranded oligonucleotides described hereinabove. The subject may be any animal, but the method is particularly suited for a human. Suitable samples are any which are believed to contain *Haemophilus ducreyi*, such as exudate from an ulcerous lesion or pus from an infected lymph node. This invention further provides a kit which is useful for the detection of *H. ducreyi* in a subject which comprises the DNA probes described hereinabove and a detectable moiety.

MATERIALS AND METHODS

Construction of an *H. ducreyi* genomic library in lambda gt11

Chromosomal DNA was isolated from five different strains of *H. ducreyi* (ATCC 27721, 27722, 33921, 33922, and type strain 33940) by the procedure of Brenner et al. (5). The purity, concentration, Tm values, and moles percent G+C contents of the DNA samples were determined by spectrophotometry and thermal denaturation with a Gilford 2400 spectrophotometer and a 2527 Thermoprogrammer (CIBA-Corning, Gilford Systems, Oberlin, Ohio).

DNA from ATCC 33922 was selected for library construction and was digested with the restriction endonuclease EcoRI (Boehringer Mannheim Biochemicals, Indianapolis, Ind.). The EcoRI fragments were fractionated on a Bio-Gel A-50m column (Bio-Rad Laboratories, Richmond, Calif.), as described by Huynh et al (22). Fractions containing EcoRI fragments of approximately 7 kilobases (kb) and smaller were pooled and then ligated to dephosphorylated lambda gt11 EcoRI arms (Promega Biotec, Madison, Wis.). The recombinant phage were packaged by using the Packagene in vitro packaging system (Promega Biotec, Madison, Wis.) and absorbed to *Escherichia coli* Y1090.

Screening of the *H. ducreyi* genomic library

Polyclonal antisera against Formalin-killed *H. ducreyi* ATCC 33922 were produced during 6 months of biweekly injections in rabbits. With fluorescent-antibody testing, the highest titer obtained was 1:2,048. This high-titer antiserum was used for library screening following absorption with an *E. coli* lysate. Recombinant phage were screened for the production of *H. ducreyi*-specific antigens by using the Express-Blot Assay Kit (Bio-Rad Laboratories) according to the directions of the manufacturer. Positive plaques were purified and then retested in the Express-Blot assay before proceeding.

Subcloning *H. ducreyi* DNA inserts into a plasmid vector

Purified plaques of antibody-reactive phage were grown on agarose plates to near-confluent lysis and the phage were allowed to diffuse in an overlay of L broth. This phage lysate was then used for DNA isolation as previously described (34). The purified DNA was digested with EcoRI, and the sizes of the *H. ducreyi* inserts were determined by agarose gel electrophoresis. DNA was transferred from the gels to nitrocellulose and hybridized with $^{32}$P-labelled *H. ducreyi* ATCC 33922 chromosomal DNA at 60° to 65° C. as described by Maniatis et al. (25). Filters were washed under stringent conditions (0.1×SSC [1×SSC is 0.15 M NaCl plus 0.015M sodium citrate] and 0.1% sodium dodecyl sulfate at 65° to 70° C.) and bound probe was then visualized by autoradiography. Three EcoRI fragments which hybridized with the probe were subcloned into dephosphorylated EcoRI-digested pUC13 and transferred to *E. coli* JM107 by transformation. Large-scale plasmid preparations were made from *E. coli* clones containing recombinant plasmids. The plasmids were then subjected to two successive purifications by ultracentrifugation on CsCl gradients.

Testing bacterial suspensions and purified DNA with the probes

The bacteria which were used for the hybridization tests are listed in FIG. 1. *H. ducreyi* isolates were grown on Casman agar with 5% rabbit blood or on Mueller-Hinton agar with 5% chocolatized horse blood, 5% fetal bovine serum, 1% IsoVitaleX, and 3 micrograms of vancomycin per ml (19, 36). *H. ducreyi* has a strong tendency to autoagglutinate. Therefore, when it was necessary to determine the number of CFU present, bacterial suspensions were grown for 24 to 48 hours in hemin broth (1), and large clumps were allowed to settle out before use. Despite these precautions, some CFU may still have originated from more than one cell. This procedure was selected because sonication or excessive vortexing of the suspensions resulted in loss of viability of *H. ducreyi*.

For testing with the probes, bacterial suspensions were blotted onto nitrocellulose in the Minifold II Slot-blotter (Schleicher & Schuell, Keene, N.H.) by using a previously described procedure (13). In some instances, the bacterial colonies were transferred directly to nitrocellulose from the agar plates. The bacteria which adhered to the filters during either procedure were lysed and the DNA was denatured as described by Maniatis et al. (25). Other samples, which included purified DNA obtained from the five ATCC strains of *H. ducreyi*, herpes simplex virus type 2-infected human embryonic lung cells, and *Treponema pallidum*-infected rabbit testicular fluid, were also applied to nitrocellulose and the DNA was denatured as described above for bacterial suspensions.

Either whole plasmids containing the *H. ducreyi* DNA inserts or the inserts alone, which had been removed from the pUC13 plasmid vector by digestion with EcoRI and then recovered from the agarose gel by using the Gene Clean procedure (Bio 101, Inc., LaJolla, Calif.), were used as probes after being labelled with $^{32}$P. Hybridization, washing and autoradiography were performed as described above.

Lesion material from rabbits

The shaved backs of rabbits were injected intradermally with $10^7$ CFU of *H. ducreyi*. The injection procedure was performed and lesion development was interpreted as previously described (15, 16, 18, 28). At 4 to 5 days following the injections, samples of exudate were removed from raised lesions and suspended in saline. A portion of each suspension was plated on Casman rabbit blood agar to recover viable organisms and applied to nitrocellulose membranes by using the slot-blot apparatus for testing with the probes.

EXPERIMENTAL RESULTS

*H. ducreyi* probes

Three DNA inserts coding for proteins which were recognized by the *H. ducreyi* antiserum were selected for subcloning into a pUC13 plasmid vector (2.7 kb). Either the whole recombinant plasmids (pLP1, 1.5-kb insert; pLP4, 5.4-kb insert; and pLP8, 5.7-kb insert) or the gel-purified inserts were used as *H. ducreyi*-specific probes (FIGS. 1 to 4). Because fragment 8, the gel purified insert from pLP8 did not hybridize to the gel-purified vector from pLP8 (pUC13), and vice versa, the inserts were considered free of residual vector DNA.

Specificity and sensitivity of the probes

Figure 4A:
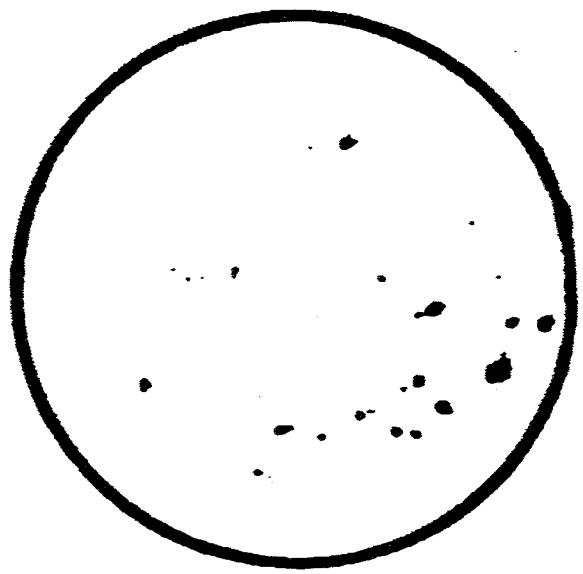
FIG. 4A and 4B show colony hybridization with pLP8 as probe. Bacterial colonies were transferred directly to nitrocellulose from agarose plates either as a mixed culture of *H. ducreyi* and other flora, from a genital ulcer (ME45)(A), or as a pure culture of *H. ducreyi* (ME38)(B). Both strains were recovered from patients in New York City in 1988.
Figure 4B:
Figure 5B:
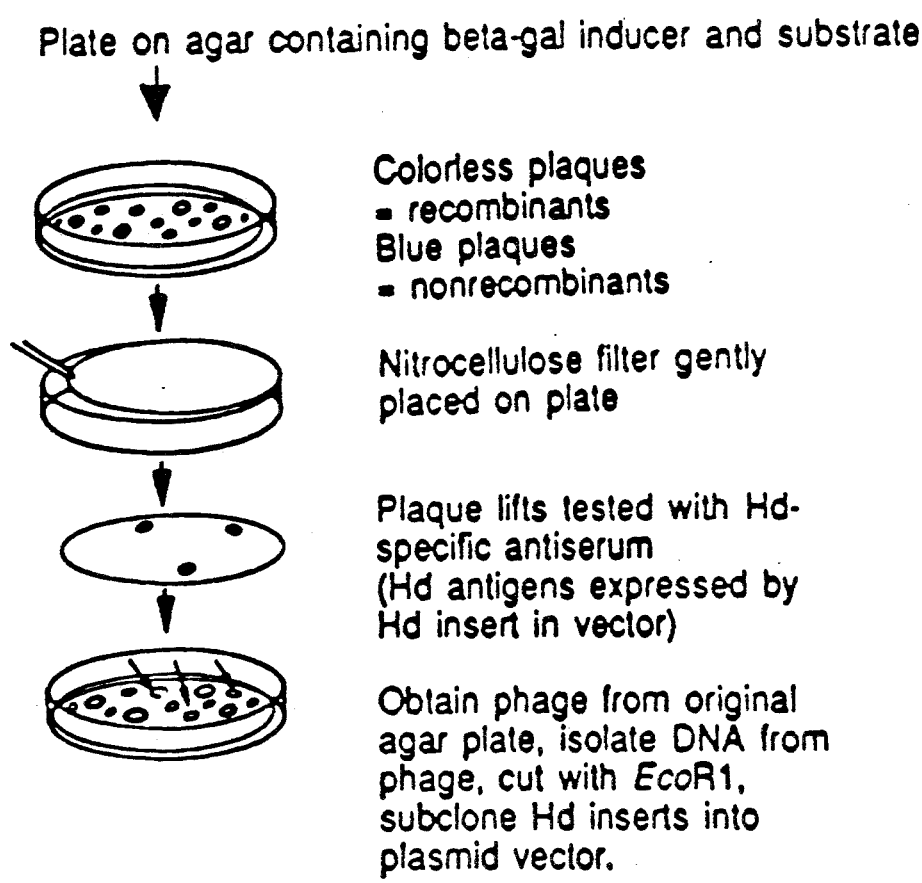
Figure 6A:
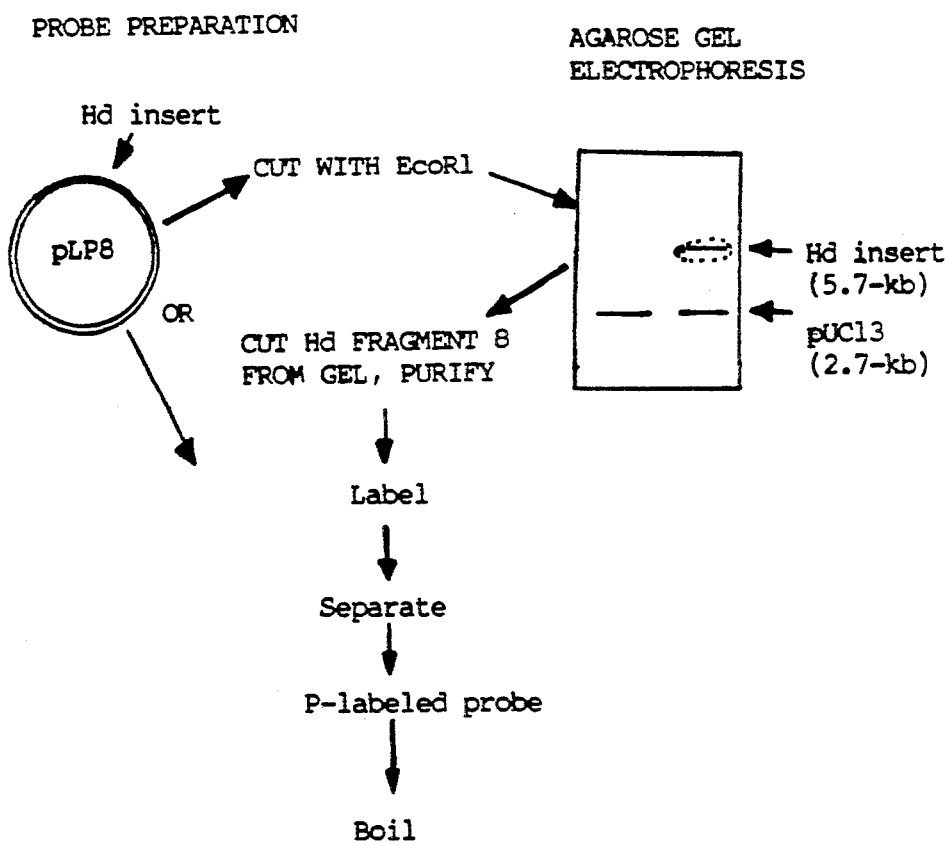
FIGS. 6A to 6C illustrate the use of DNA probes for *H. ducreyi* detection.
Figure 6B:
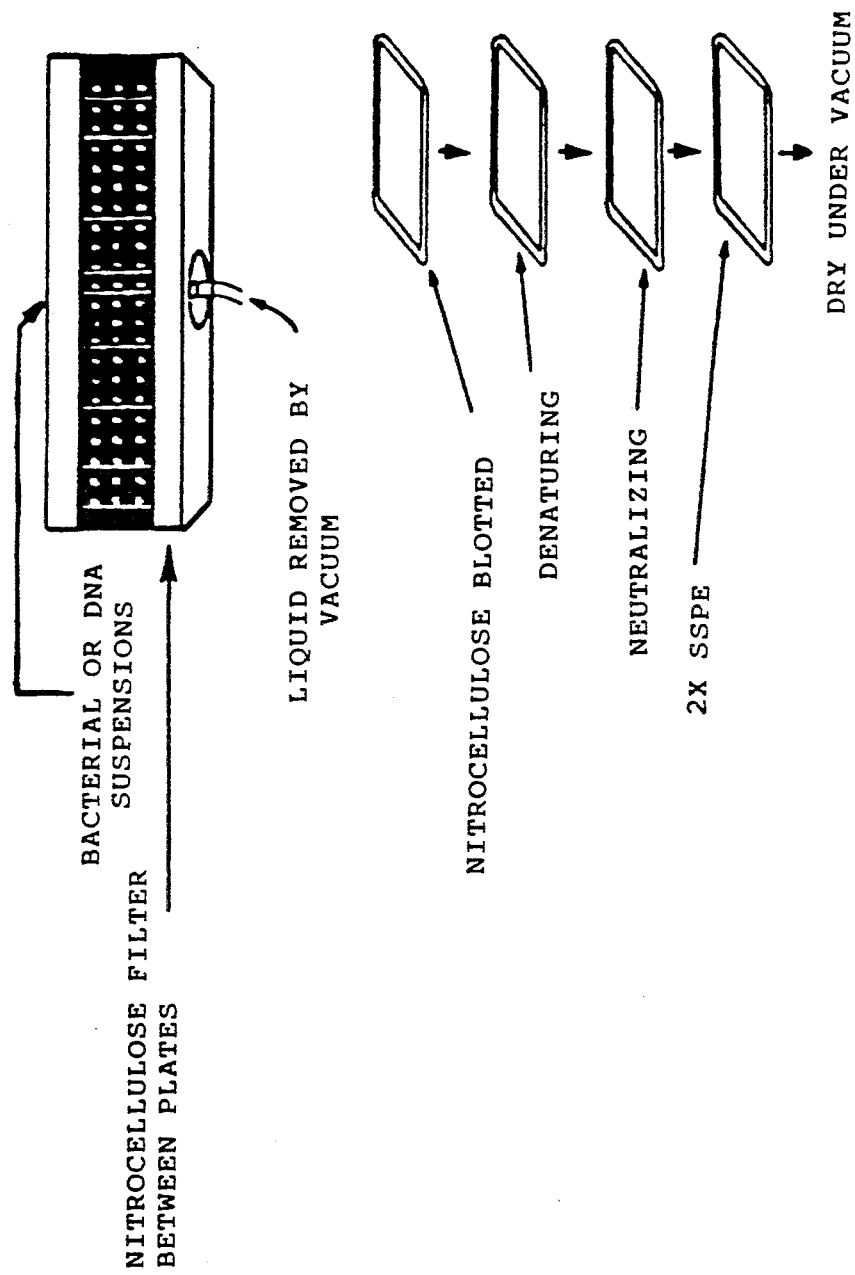
Figure 6C:
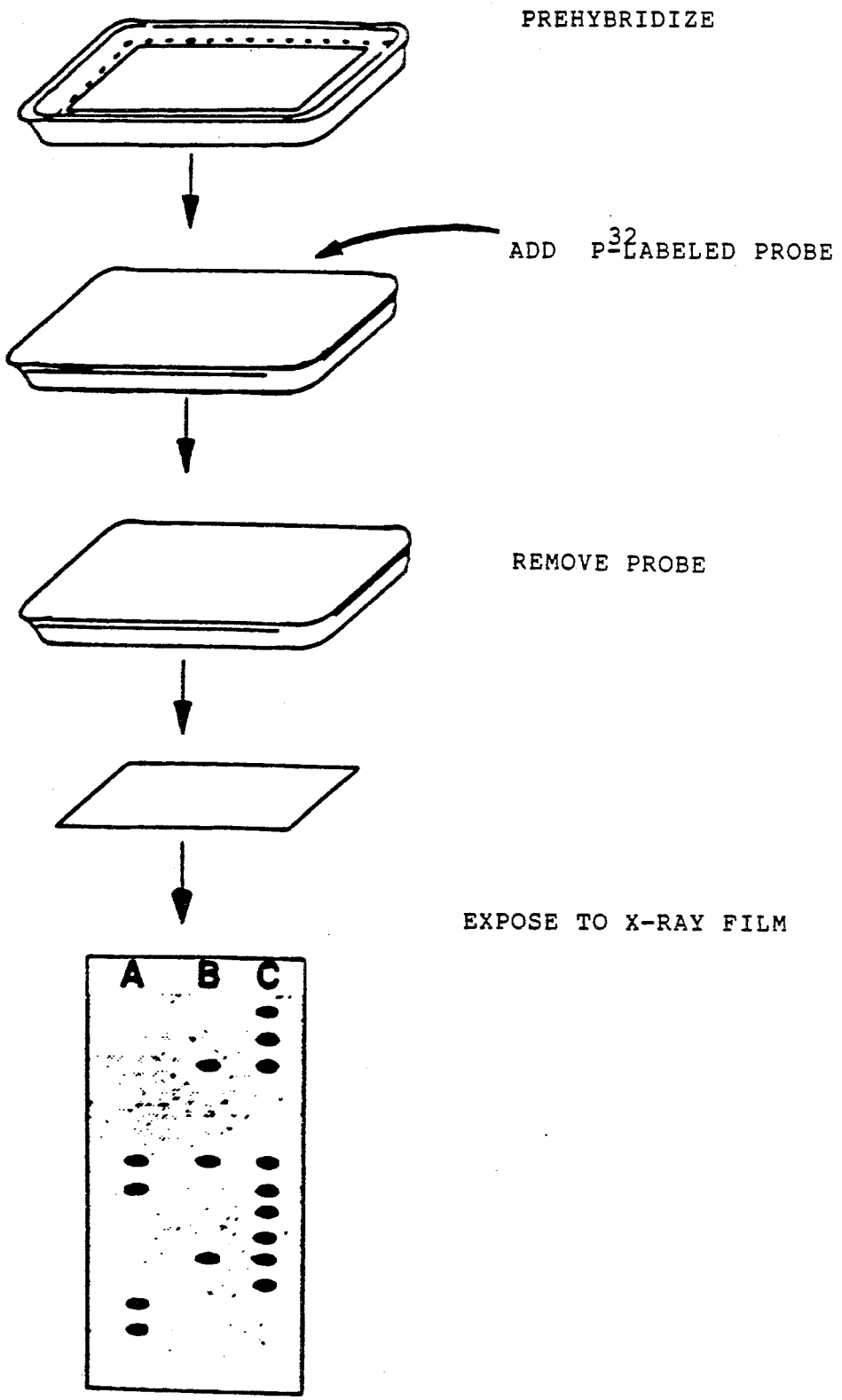

FIG. 1 lists the organisms tested and the results obtained using the three probes. All strains of *H. ducreyi* reacted strongly with the probes (FIG. 1), as did the purified DNA from all five ATCC strains. Nine recent isolates of *H. ducreyi* cultured from patients in 1988 by the New York City Department of Health were tested in the slot-blot apparatus and also by blotting colonies directly from plates onto nitrocellulose. All were found to be positive in pure and mixed cultures (FIGS. 1 and 4). The other significant genital pathogens, *Neisseria gonorrhoeae*, herpes simplex virus type 2, and *T. pallidum*, were all completely nonreactive with the probes.

Weak cross-reactivity was seen with the other Haemophilus species and with three of the four Pasteurella species when $3.0 \times 10^7$ to $6 \times 10^7$ CFU was tested. FIG. 3 illustrates the intensity of the homologous reactions versus the heterologous reactions. When suspensions of the cross-reacting organisms were diluted and probed, the weak reactions were no longer seen with $10^5$ to $10^6$ CFU or less while this same number of *H. ducreyi* still reacted strongly.

The three probes consistently detected $10^4$ CFU of *H. ducreyi* in pure or mixed culture and produced a weak signal when $10^3$ CFU was present (FIG. 2).

Probing lesion material from rabbits

Four strains of *H. ducreyi* (ATCC 33922; ATCC 33940; CDC 542; and a recent clinical isolate from New York City, ME 38) were used to inject rabbits intradermally. All four strains produced necrotic lesions. Within 2.5 to 3 weeks, the lesions had healed. From the exudates obtained from the lesions 4 to 5 days following injection of 10⁷ organisms, only CDC 542 could be recovered by culture. However, by using fragment 8 as a probe, *H. ducreyi* DNA could be detected as a weak to 1+ signal in exudate from lesions produced by all four strains. The hybridization with the *H. ducreyi* probe was specific, since purified pUC13 used as a probe did not hybridize nonspecifically to the rabbit lesion samples.

EXPERIMENTAL DISCUSSION

In analyzing DNA from *H. ducreyi* ATCC stains used in this study, $T_m$ values were obtained (85.1° to 85.6° C.) and G+C content values (37.9 to 39.0 mol %) which agreed with those previously reported. Killian (23) had determined the average G+C content for two strains of *H. ducreyi* to be 37.8 mol % and Piechulla et al. (29) had found average $T_m$ and G+C content values of 85.1° C. and 37.8 mol %, respectively, for two *H. ducreyi* ATCC strains.

The DNA probes constructed from ATCC 33922 are relatively specific for *H. ducreyi*. They react strongly with the DNA from the other ATCC strains and with all 16 *H. ducreyi* isolates tested. When 37 other bacterial isolates, including organisms likely to be encountered in the urogenital tract were tested with the probes, 28 were completely negative and 9 (*Haemophilus haemolyticus*; *H. influenzae*, types A and B; *H. influenzae*, nontypeable, biotyes III and V; *Haemophilus parainfluenzae*; *Pasteurella gallinarum*; *Pasteurella multocida*; and *Pasteurella pneumotropica*) reacted weakly, even though a large number of organisms ($10^7$ CFU) was used. No reactions were seen with these organisms when $10^5$ to $10^6$ CFU was tested. In contrast, this number of *H. ducreyi* still reacted strongly with the probes.

In testing bacterial suspensions and purified DNA with the probes, we have consistently seen strong positive reactions (FIGS. 3 and 4) only with *H. ducreyi*. Moreover, the reactions have been seen with all strains of *H. ducreyi* tested.

The presence of areas of homology between the weakly reactive organisms and *H. ducreyi* is not surprising since antigenic cross-reactivity between *H. ducreyi* and other Haemophilus species has been reported by others (32, 33) and has been seen in fluorescent-antibody tests which have been performed. Also, the G+C contents of all members of the genus Haemophilus are similar (23). (However, DNA-DNA hybridization has shown that *H. ducreyi* is only slightly similar to all other Haemophilus species [0 to 6% related] [2, 7] and quinones extracted from bacterial membranes have been found to differ significantly between *H. ducreyi* and other Haemophilus species [6]). Pasteurella species may also share small areas of DNA relatedness with the cloned *H. ducreyi* sequences, since both Pasteurella and Haemophilus species are members of the family Pasteurellaceae.

By using any one of the three DNA probes, $10^4$ CFU of *H. ducreyi* was consistently detected in pure or mixed cultures. A weak signal was usually seen even when only $10^3$ CFU was present. These results demonstrate both the sensitivity and specificity of the probes for *H. ducreyi*, as only this organism could be detected a these dilutions.

The probes were also able to detect four different strains of *H. ducreyi* in rabbit lesion exudate, while only one could be recovered by culture. *H. ducreyi* lesions do not ulcerate in rabbits but instead become dry, indurated and heal fairly quickly (16). Investigators have reported the recovery of *H. ducreyi* from rabbit lesions only at 24, 48, and 72 hours postinfection (16, 18). These observations suggest that organisms do not survive long in this particular host tissue. In the present study, three of the four samples were obtained when the organisms were no longer viable, however, sufficient DNA was still present so that detectable hybridization could occur.

Nucleic-acid hybridization using radiolabelling has previously been reported to be sensitive enough to detect homogenous sequences in about $10^2$ to $10^6$ bacteria (17). The ability to detect *H. ducreyi* by the method of this invention is well within this range. However, increased sensitivity may be necessary in order to detect the low numbers of organisms which might be present in some clinical specimens. Detection of a small amount of *H. ducreyi* DNA can be achieved by amplification either of total DNA or of only the target sequence homologous to the probe. The most direct approach would involve amplification of the total DNA by growth of the organism. By this method, as few as 10 organisms could be amplified to a detectable level in 10 doubling times. However, if the organisms were no longer viable, the polymerase chain reaction, with specific primers and a thermostable polymerase (31) could be used.

The use of these specific DNA probes for accurate laboratory diagnostic tests will ensure more rapid and accurate identification of *H. ducreyi*.

REFERENCES

1. Abeck, D., A. P. Johnson, R. C. Ballard, Y. Dangor, E. A. Fontaine, and D. Taylor-Robinson. 1987. Effect of cultural conditions on the protein and lipopolysaccharide profiles of *Haemophilus ducreyi* analysed by SDS-PAGE. FEMS Micro-biol. Lett. 48:397-399.
2. Albritton, W. L., J. K. Setlow, M. Thomas, F. Sottnek, and A. G. Steigerwalt. 1984. Heterospecific transformation in the genus Haemophilus. Mol. Gen. Genet. 193:358-363.
3. Becker, T. M., W. DeWitt, and G. VanDusen. 1987. *Haemophilus ducreyi* infection in South Florida: a rare disease on the rise? South. Med. J. 80:182-184.
4. Blackmore, C. A., K. Limpakarnjanarst, J. G. Rigau-Perez, W. L. Albritton, and J. R. Greenwood. 1985. An outbreak of chancroid in Orange County, California: descriptive epidemiology and disease-control measures. J. Infect. Dis. 151:840-844.
5. Brenner, D. J., A. C. McWhorter, J. K. L. Knutson, and A. G. Steigerwalt. 1982. *Escherichia vulneris*: a new species of Enterobacteriaceae associated with human wounds. J. Clin. Micro-biol. 15:1133-1140.
6. Carione, G. M., W. O. Schalla, C. W. Moss, D. L. Ashley, D. M. Fast, J. S. Holler, and B. D. Plikaytis. 1988. *Haemophilus ducreyi* isoprenoid quinone content and stucture determination. Int. J. Syst. Bacteriol. 38:249-253.
7. Casin, I. F. Grimont, P. A. D. Grimont, and M. Sanson-Le Pors. 1985. Lack of deoxyribonucleic acid relatedness between *Haemophilus ducreyi* and other Haemophilus species. Int. J. Syst. Bacteriol. 35:23-25.
8. Centers for Disease Control. 1982 Chancroid-California. Morbid. Mortal. Weekly Rep. 31:173-175.
9. Centers for Disease Control. 1985. Chancroid-Massachussets. Morbid. Mortal Weekly Rep. 34:711-718.
10. Centers for Disease Control. 1985. Sexually transmitted disease statistics. Issue no. 135. Centers of Disease Control, Atlanta.

11. Center for Disease Control. 1987. Sexually transmitted disease statistics. Issue no. 136. Centers for Disease Control, Atlanta.
12. Dangor, Y., S. D. Miller, F. da la Exposito, and H. J. Koornhof. 1988. Antimicrobial susceptibilities of southern African isolates of Haemophilus ducreyi. Antimicrob. Agents Chemother. 32:1458–1460.
13. Davis, L. G., M. D. Dibner, and J. F. Battey. 1986. Basic methods in molecular biology. Elsevier Science Publishing, Inc. New York.
14. Denys, G. A., T. A. Chapel, and C. D. Jeffries. 1978. An indirect fluorescent antibody technique for Haemophilus ducreyi. Health Lab. Sci. 15:128–132.
15. Dienst, R. B. 1948. Virulence and antigenicity of Haemophilus ducreyi. Am. J. Syph. Gonnorrhea Vener. Dis. 32:289–291.
16. Felner, R. R., and F. Mortara. 1945. Infectivity of Haemophilus ducreyi for the rabbit and the development of skin hypersensitivity. Am. J. Syph. Gonorrhea Vener. Dis. 29:71–79.
17. Fung-Tome, J. C., and R. C. Tilton. 1988. Application of nucleic acid hybridization in clinical bacteriology, p. 238–244. In K. Wicher (ed), Microbiol. antigenodiagnosis, vol. 1. CRC Press, Inc., Boca Raton, Fla.
18. Hammond, G. W., C. J. Lian, J. C. Wilt, and A. R. Ronald. 1978. Antimicrobial susceptibility of Haemophilus ducreyi. Antimicrob. Agents Chemother. 13:608–612.
19. Hammond, G. W., C. J. Lian, J. C. Wilt, and A. R. Ronald. 1978. Comparison of specimen collection and laboratory techniques of isolation of Haemophilus ducreyi. J. Clin. Microbiol. 7:39–43.
20. Hammond, G. W., M. Slutchuk, J. Scatliff, E. Sherman, J. Wilt, and A. R. Ronald. 1980. Epidemiologic, clinical, laboratory, and therapeutic features of an urban outbreak of chancroid in North America. Rev. Infect. Dis. 2:867–879.
21. Health and Welfare, Canada. 1988. Chancroid outbreak—Winipeg, Manitoba. Can. Dis. Weekly Rep. 14:13–15.
22. Huynh, T. V., R. A. Young, and R. W. Davis. 1985. Construction and screening cDNA libraries in lambda gt10 and lambda gt11 p. 49–77. In D. M. Glover (ed.), DNA cloning: a practical approach, vol. 1. IRL Press, Washington, D.C.
23. Kilin, M. 1976. A taxonomic study of the genus Haemophilus with the proposal of a new species. J. Gen. Microbiol. 93:9–62.
24. Kreiss, J. K., D. Koech, F. A. Plummer, K. K. Holmes, Lightfoote, P. Piot, A. R. Ronald, J. O. Ndinya-Achola, L. D'Costa, P. Roberts, E. N. Ngugi, and T. C. Quinn. 1986. AIDS virus infection in Nairobi prostitutes: spread of the epidemic East Africa. N. Engl. J. Med. 314:414–418.
25. Manaitis, T., E. F. Fritsch, and J. Sambrook. 1982. Molecular cloning: a laboratory manual. Cold Spring Harbor Laboratory and Cold Spring Harbor, N.Y.
26. Musey, K., E. Van Dyck, T. Vervoort, D. Taylor, C. Hoge, P. Piot. 1988. Use of an enzyme immunoassay to detect sero IgG antibodies to Haemophilus ducreyi. J. Infect. Dis. 152:1039–1043.
27. New York City Department of Health. 1987. Treatment chancroid with ceftriaxone: New York City Health Information. 6:1–2.
28. Odumeru, J. A., G. M. Wiseman, and A. R. Ronald. 1984. Virulence factors of Haemophilus ducreyi. Infect. Immuno. 43:607–611.
29. Piechulla, K., R. Mutters, S. Burbach, R. Klussmeier, S. Pohl and W. Mannheim. 1986. Deoxyribonucleic acid relationships "Histophilus ovis/Haemophilus sommus," Haemophilus heamoglobinophilus and "Actinobacllus seminis." Int. J. Sys. Bacteriol. 36:1–7.
30. Quinn. T. C., J. M. Mann, J. W. Curran, and P. Piot. 1986. AIDS in Africa: an epidemiologic paradigm. Science. 234:955–963.
31. Saiki, R. K., D. H. Gelfand, S. Stoffel, S. J. Scharf, R. Higudius, G. T. Horn, K. B. Mullis, and H. A. Erlich. 1988. Primer directed enzymatic amplificaton of DNA with a thermostable DNA polymerase. Science. 239:487–491.
32. Saunders, J. M., and J. D. Folds. 1986. Immunoblot analysis of antigens associated with Haemophilus ducreyi using serum from immunized rabbits. Genitourin. Med. 62:321–328.
33. Schalla, W. O., L. L. Sanders, G. P. Schmid, M. R. Tam, and S. A. Morse. 1986. Use of dot-immunobinding and immunofluorescence assays to investigate clinically suspected cases of chancroid. J. Infect. Dis. 153:879–887.
34. Silhavy, T. J., M. L. Berman, and L. W. Enquist. 1984. Experiments with gene fusions. Cold Spring Harbor Laboratory, Cold Spring Harbor, N.Y.
35. Simonsen, J. N., D. W. Cameron, M. N. Gakinya, J, Ndinya-Achola, L. J. D'Costa, P. Karasira, M. Cheang, A. Ronald, P. Plot, and F. A. Plummer. 1988. Human immunodeficiency virus infection among men with sexually transmitted diseases: experience from a center in Africa. N. Engl. J. Med. 319:274–278.
36. Sottnek, F. O., J. W. Biddle, S. J. Kraus, R. E. Weaver, and J. A. Stewart. 1980. Isolation and identification of Haemophilus ducreyi in a clinical study. J. Clin. Microbiol. 12:170–174.
37. Stuttgen, G. 1981. Ulcus molle: chancroid. Grosse Ver. Berlin, Federal Republic of Germany.
38. Tchen, et al. 1989. Probe and process for the detection of specific microorganisms, particularly legionellas, in environments which contain them. U.S. Pat. No. 4,810,644.
39. Litman, et al. 1983. Macromolecular environment control in specific receptor assays. U.S. Pat. No. 4,374,925.
40. Kettman, et al. 1988. Methods for diagnosing syphylis. U.S. Pat. No. 4,740,467.

What is claimed is:

1. A nucleic acid probe consisting essentially of a nucleic acid sequence corresponding to ATCC No. 68008, or ATCC No. 68009, or ATCC No. 68010 which specifically hybridizes to Haemophilus ducreyi DNA.

2. The recombinant plasmid designated pLP1 (ATCC No. 68008).

3. The recombinant plasmid designated pLP4 (ATCC No. 68009).

4. The recombinant plasmid designated pLP8 (ATCC No. 68010).

5. The DNA probe as in claim 1 labelled with a detectable moiety.

6. The DNA probe as in claim 5 wherein the detectable moiety is a radioisotope.

7. The DNA probe as in claim 6 wherein the radioisotope is $^{32}P$.

8. A kit which is useful for the detection of Haemophilus ducreyi in a sample which contains the DNA probe as in claim 1 and detectable moieties.

9. The DNA probe as in claim 5, wherein the DNA probe has been denatured so as to form a labelled single stranded DNA probe.

10. A method of detecting in a subject the presence of *Haemophilus ducreyi* which comprises:
(a) obtaining a suitable sample suspected of containing *Haemophilus ducreyi* from the subject;
(b) isolating and denaturing the nucleic acid in the sample so as to produce single stranded nucleic acid molecules;
(c) contacting the single stranded nucleic acid molecule of step (b) with the probe as in claims 5 or 9 under suitable conditions permitting hybridization of complementary single stranded molecules; and
(d) detecting the presence of hybridized molecules so formed, whereby the presence of *Haemophilus ducreyi* in the subject is detected.

11. The method as in claim 10 wherein the subject is an animal.

12. The method as in claim 10 wherein the subject is a human.

13. The method as in claim 10 wherein the sample comprises exudate from an ulcer.

14. The method as in claim 10 wherein the sample comprises pus from an infected lymph node.

15. The method as in claim 10 which further comprises amplifying the total DNA in the sample.

16. The method as in claim 10 which further comprises enzymatically amplifying DNA in the sample which is complementary to the probe.

* * * * *